United States Patent
Kawano et al.

(10) Patent No.: US 9,366,614 B2
(45) Date of Patent: Jun. 14, 2016

(54) POROSITY MEASURING DEVICE AND POROSITY MEASURING METHOD

(75) Inventors: Makoto Kawano, Suita (JP); Hitoshi Watarai, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 354 days.

(21) Appl. No.: 14/237,153

(22) PCT Filed: Aug. 2, 2012

(86) PCT No.: PCT/JP2012/069697
§ 371 (c)(1),
(2), (4) Date: Feb. 4, 2014

(87) PCT Pub. No.: WO2013/021910
PCT Pub. Date: Feb. 14, 2013

(65) Prior Publication Data
US 2014/0174157 A1    Jun. 26, 2014

(30) Foreign Application Priority Data

Aug. 5, 2011 (JP) ................................. 2011-171650

(51) Int. Cl.
*G01N 15/08* (2006.01)
*G01N 15/10* (2006.01)

(52) U.S. Cl.
CPC .............. *G01N 15/08* (2013.01); *G01N 15/088* (2013.01); *G01N 15/1031* (2013.01)

(58) Field of Classification Search
CPC .. G01N 15/08; G01N 15/088; G01N 15/1031
USPC ............................................................ 73/38
See application file for complete search history.

(56) References Cited

U.S. PATENT DOCUMENTS

2003/0199228 A1* 10/2003 Kennedy ............... B24B 37/048
451/11
2004/0018611 A1* 1/2004 Ward .................... B82Y 15/00
435/287.2

FOREIGN PATENT DOCUMENTS

JP      07-249218 A    9/1995
JP      09-089750 A    4/1997

(Continued)

OTHER PUBLICATIONS

M. Suwa et al., "Magnetic Susceptibility Measurement of Single Micro-Particle by Magnetophoretic Velocimetry", Journal of Japan Society for Analytical Chemistry, 2010, vol. 59, No. 10, pp. 895-902.

(Continued)

*Primary Examiner* — Hezron E Williams
*Assistant Examiner* — Rodney T Frank
(74) *Attorney, Agent, or Firm* — Studebaker & Brackett PC

(57) ABSTRACT

A porosity measuring device (10) according to the present invention includes a magnetic field generating section (20), a dispersoid measuring section (30) configured to measure movement of a dispersoid (s) dispersed in a dispersion medium (m) in a state where a magnetic field is generated by the magnetic field generating section (20), and an operating section (40) configured to obtain a porosity of the dispersoid (s) on the basis of a measurement result of the dispersoid measuring section (30). The operating section (40) obtains a magnetophoretic velocity of the dispersoid (s) from the measurement result of the dispersoid measuring section (30). The operating section (40) preferably obtains the magnetophoretic velocity of the dispersoid (s) from the measurement result of the dispersoid measuring section (30).

7 Claims, 13 Drawing Sheets

(56) References Cited

FOREIGN PATENT DOCUMENTS

| JP | 11-229232 A | 8/1999 |
|---|---|---|
| JP | 2002-022704 A | 1/2002 |
| JP | 2002-071645 A | 3/2002 |
| JP | 2004-138464 A | 5/2004 |
| JP | 2007-271329 A | 10/2007 |
| JP | 4300317 B2 | 5/2009 |
| JP | 4318183 B2 | 6/2009 |
| JP | 2010-167391 A | 8/2010 |
| JP | 4599538 B2 | 10/2010 |

OTHER PUBLICATIONS

C.B. Fuh et al., Journal of Chromatography A, 923 (2001) 263-270, "Particle magnetic susceptibility determination using analytical split-flow thin fractionation".

N. Pamme et al., Anal. Chem. 2004, 76, 7250-7256, "On-Chip Free-Flow Magnetophoresis: Continuous Flow Separation of Magnetic Particles and Agglomerates".

International Search Report; PCT/JP2012/069697; Oct. 30, 2012.

The extended European search report issued by the European Patent Office on Jan. 23, 2015, which corresponds to European Patent Application No. 12822219.7-1553 and is related to U.S. Appl. No. 14/237,153.

Masayori Suwa et al.; "Magnetophoretic Velocimetry of Manganese (II) in a Single Emulsion Droplet at the Femtomole Level"; Analytical Chemistry; Nov. 1, 2001; pp. 5214-5219; vol. 73; No. 21.

Mariko Arase et al.; "Sensitive light-scattering detection-magnetophoretic acceleration mass analysis of single microparticles in an atmosphere"; Analytical and Bioanalytical Chemistry; 2008; pp. 701-707; vol. 391.

Hitoshi Watarai et al.; "Magnetophoresis and electro-magnetophoresis of microparticles in liquids"; Analytical and Bioanalytical Chemistry; 2004; pp. 1693-1699; vol. 378.

\* cited by examiner

POROSITY MEASURING DEVICE AND POROSITY MEASURING METHOD

TECHNICAL FIELD

The present invention relates to porosity measuring devices and porosity measuring methods.

BACKGROUND ART

As methods for measuring the porosity of a sample of particle powder, there are known a gas adsorption method and a mercury injection method. In these methods, the surface area of the sample in a dried state is evaluated, and then, the average porosity of the sample is calculated according to the relationship with the average grain diameter or the mass (see Patent Literatures 1 and 2, for example). A method of measuring an average porosity using NMR is also known.

CITATION LIST

Patent Literature

[PTL 1] Japanese Patent Application Laid-Open Publication No. 07-249218

[PTL 2] Japanese Patent Application Laid-Open Publication No. 11-229232

SUMMARY OF INVENTION

Technical Problem

However, none of the aforementioned methods can measure the porosity of each individual particle. In view of this, the present inventor found a novel scheme capable of measuring the porosity of each particle one by one using the magnetic susceptibility.

The present invention has been made in view of the above problems and has its object of providing a porosity measuring device and a porosity measuring method which are capable of measuring the porosity of each of dispersoids dispersed in a dispersion medium.

Solution to Problem

A porosity measuring device according to the present invention includes: a magnetic field generating section; a dispersoid measuring section configured to measure movement of a dispersoid dispersed in a dispersion medium in a state where a magnetic field is generated by the magnetic field generating section; and an operating section configured to obtain a porosity of the dispersoid on the basis of a measurement result of the dispersoid measuring section.

In one embodiment, the operating section obtains a magnetophoretic velocity of the dispersoid from the measurement result of the dispersoid measuring section.

In one embodiment, the operating section obtains a volume susceptibility of the dispersoid from the magnetophoretic velocity of the dispersoid and obtains the porosity of the dispersoid from the volume susceptibility of the dispersoid.

In one embodiment, the dispersoid measuring section includes: an optical lens configured to magnify the dispersoid dispersed in the dispersion medium; and an imaging section configured to image the dispersoid magnified by the optical lens.

In one embodiment, the magnetic field generating section is configured to generate the magnetic field so that a position of the dispersoid dispersed in the dispersion medium differs according to a volume susceptibility of the dispersoid.

A porosity measuring method according to the present invention includes: measuring movement of a dispersoid dispersed in a dispersion medium in a state where a magnetic field is generated; and obtaining a porosity of the dispersoid on the basis of a measurement result of the movement of the dispersoid.

In one embodiment, the obtaining a porosity of the dispersoid includes obtaining a magnetophoretic velocity of the dispersoid from the measurement result of the movement of the dispersoid.

In one embodiment, the obtaining a porosity of the dispersoid includes: obtaining a volume susceptibility of the dispersoid from the magnetophoretic velocity of the dispersoid; and obtaining the porosity of the dispersoid from the volume susceptibility of the dispersoid.

In one embodiment, in the measuring movement of the dispersoid, the magnetic field is generated so that a position of the dispersoid dispersed in the dispersion medium differs according to a volume susceptibility of the dispersoid.

In one embodiment, the dispersoid includes a silica gel particle.

In one embodiment, the dispersion medium includes acetonitrile.

Advantageous Effects of Invention

According to the present invention, the porosity of each of the dispersoids dispersed in the dispersion medium can be measured.

DESCRIPTION OF EMBODIMENTS

Embodiments of a porosity measuring device according to the present invention will be described below with reference to the accompanying drawings. However, the present invention is not limited to the following embodiments.

Figure 1:
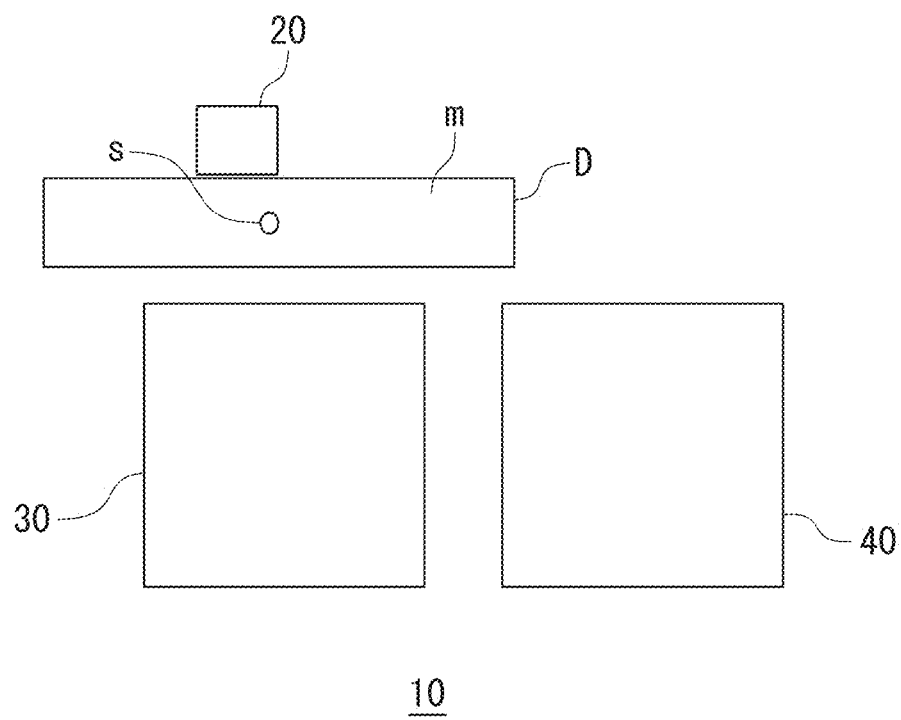
FIG. 1 is a schematic illustration of one embodiment of a porosity measuring device according to the present invention.

FIG. 1 is a schematic illustration showing a porosity measuring device 10 of the present embodiment. The porosity measuring device 10 includes a magnetic field generating section 20, a dispersoid measuring section 30, and an operating section 40. A dispersion system D in which a dispersoid s is dispersed into a dispersion medium m is arranged in the vicinity of the magnetic field generating section 20. The dispersion system D is put in a tubular member, for example. When the magnetic field generating section 20 generates a magnetic field in the dispersion system D, the dispersoid s moves in a predetermined direction. This phenomenon is called magnetophoresis.

The dispersoid measuring section 30 measures the movement of the dispersoid s in a state where a magnetic field is generated by the magnetic field generating section 20. It is noted that the dispersoid measuring section 30 may be merely referred to as a measuring section 30 in the following description.

It is further noted that although FIG. 1 shows only one dispersoid s in the dispersion medium m, a plurality of dispersoids s may be present in the dispersion medium m, of course. The dispersion medium m may be liquid or gas. For example, the dispersion medium m may be acetonitrile. Alternatively, the dispersion medium m may be methanol or water. Or, the dispersion medium may be air, for example. In addition, the dispersoid s may be particulate(s). Alternatively, the dispersoid s may be a cell (e.g., a red blood cell). The dispersoid s has a diameter of 10 nm or larger, preferably 100 nm or larger and 100 μm or smaller. It is noted that when the specific gravity of the dispersoid s is equal to or more than twice that of the dispersion medium m, the dispersoid s sediments comparatively quickly. In this case, it is preferable to change the dispersion medium m to one with a comparatively high specific gravity or to allow the dispersion medium m to flow by a pump or the like. Further, in addition to flowage by the pump, preferably, the measurement system (direction of magnetophoresis by the magnetic field generating section 20 and direction in which the dispersion system D extends) is arranged in the vertical direction to measure velocity change by the magnetic field relative to gravity drop of the dispersoid s.

The magnetic susceptibility of the dispersoid s is different from the magnetic susceptibility of the dispersion medium m. Accordingly, generation of the magnetic field makes the dispersoid s to move in the predetermined direction. The degree of movement of the dispersoid s depends on the magnitude of the magnetic field.

The operating section 40 obtains the porosity of the dispersoid s on the basis of the measurement result of the measuring section 30. As will be described later in detail, the operating section 40 obtains the magnetophoretic velocity of the dispersoid s from the measurement result of the measuring section 30, for example. In this case, the operating section 40 may obtain the magnetophoretic velocity of the dispersoid s from time variation in position information indicative of the position of the dispersoid s measured by the measuring section 30. Referring to one example thereof, the measuring section 30 may image the dispersoid s at predetermined regular time intervals, and the operating section 40 obtains the magnetophoretic velocity of the dispersoid s from these imaged results.

Thereafter, the operating section 40 obtains the porosity of the dispersoid s from the magnetophoretic velocity of the dispersoid s. Specifically, the operating section 40 obtains the volume susceptibility of the dispersoid s from the magnetophoretic velocity of the dispersoid s and obtains the porosity of the dispersoid s from the volume susceptibility of the dispersoid s. As the operating section 40, a personal computer may be used, for example.

With the porosity measuring device 10, the porosity of the dispersoid s can be obtained directly from the movement of the single dispersoid s, thereby achieving measurement of the porosity of each dispersoid s. Further, the uniformity in porosity of a plurality of dispersoids s dispersed in the dispersion medium m can be inspected.

It is noted that the porosity measured by the porosity measuring device 10 not only is defined simply by the shape of the dispersoid s but also serves as an index indicating the relationship between the dispersoid s and the dispersion medium m. For example, even assuming that the dispersoid s is the same, different dispersion media m may result in different porosities. For this reason, the state of the dispersion medium infiltrating into the dispersoid s can be grasped according to the porosity. It is noted that the dispersoid s may be dispersed in the dispersion medium m to be swollen.

The movement of the dispersoid s is determined according to each volume susceptibility of the dispersoid s and the dispersion medium m. It is noted that volume susceptibility is a parameter depending on the electronic state and serves as a physically highly reliable index. Further, with the porosity measuring device 10, information on the inside and the surface of the dispersoid s can be obtained without breaking the dispersoid s.

A porosity measuring method according to the present embodiment will be described below with reference to FIG. 2.

Figure 2A:
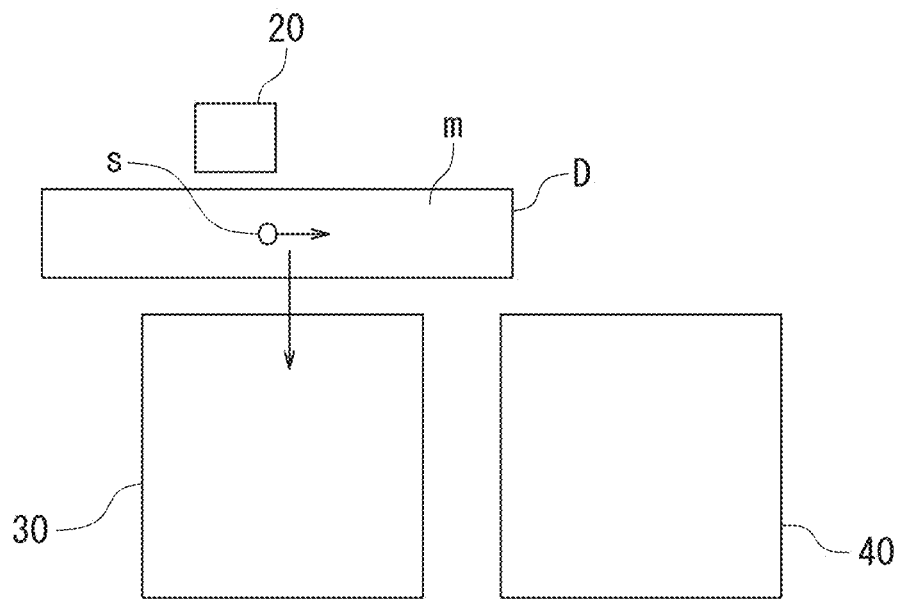
FIGS. 2A and 2B are schematic illustrations for explaining a porosity measuring method according to the present invention.

First, as shown in FIG. 2A, the movement of the dispersoid s dispersed in the dispersion medium m is measured in a state where the magnetic field is generated. For example, the magnetophoretic velocity of the dispersoid s can be obtained from the movement of the dispersoid s.

Figure 2B:
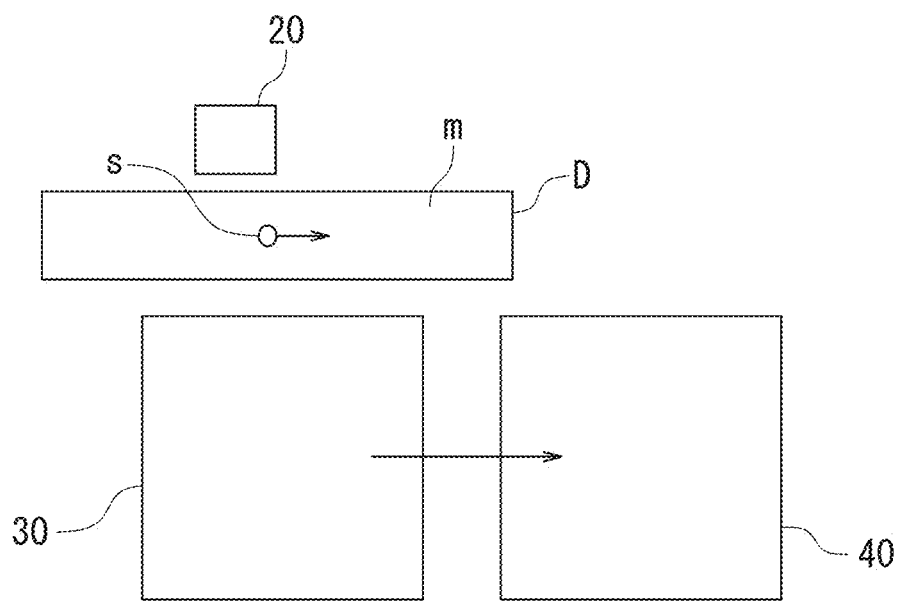

Next, as shown in FIG. 2B, the porosity of the dispersoid s is obtained on the basis of the measurement result of the movement of the dispersoid s. For example, the volume susceptibility of the dispersoid s is obtained from the movement of the dispersoid s, and then, the porosity of the dispersoid s is obtained from the volume susceptibility of the dispersoid s.

In this way, the porosity of the dispersoid s can be measured by utilizing the magnetophoresis of the dispersoid s without breaking the dispersoid s. It is noted that the dispersoid s may be a magnetic particle used for ink toner. Alternatively, the dispersoid s may be a material used for cosmetics (e.g., foundation) or a material applied to any drag delivery systems (DDS). It is further noted that the dispersoid s may be a cell, as described above. In the case where the dispersoid s is a cell, the shape of the dispersoid s may vary as time advances.

The movement of the dispersoid s will be described below with reference to FIG. 3. Preferably, the magnetic field generating section 20 may generate a strong magnetic field with a large magnetic field gradient by pole pieces, for example.

Figure 3A:
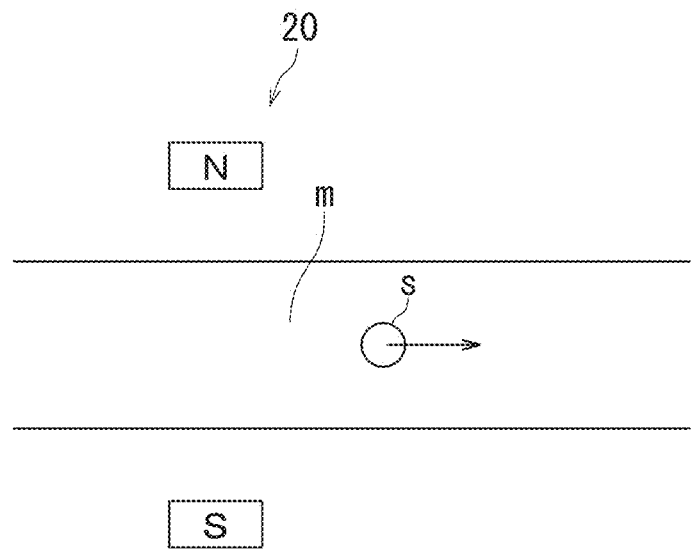
FIGS. 3A and 3B are schematic illustrations for explaining the relationship between the volume susceptibilities of a dispersoid and a dispersion medium and the movement direction of the dispersoid in a porosity measuring device of the present embodiment.

When the volume susceptibility of the dispersoid s is smaller than that of the dispersion medium m, the dispersoid s moves in the direction away from the magnetic field, as shown in FIG. 3A. It is noted that the dispersoid s receives force in the vicinity of each end of the magnets. For example, the dispersoid s receives the force in the vicinity of each end of the magnets in the range of about ±200 μm.

Figure 3B:
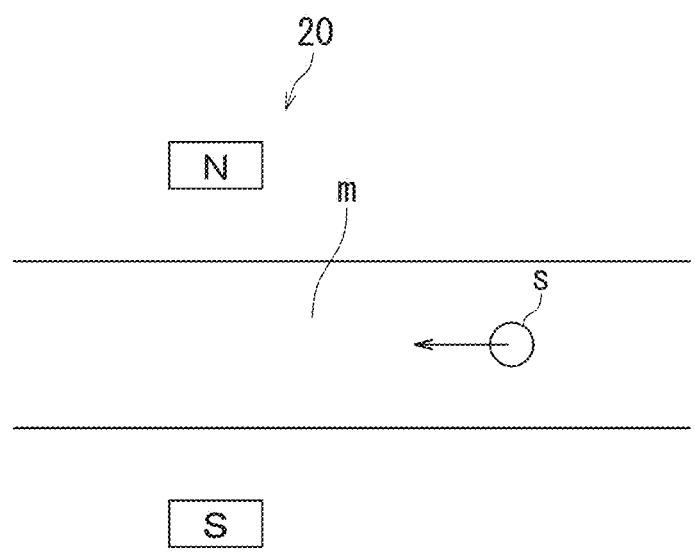

When the volume susceptibility of the dispersoid s is larger than that of the dispersion medium m, the dispersoid s moves in the direction close to the magnetic field, as shown in FIG. 3B.

Figure 4:
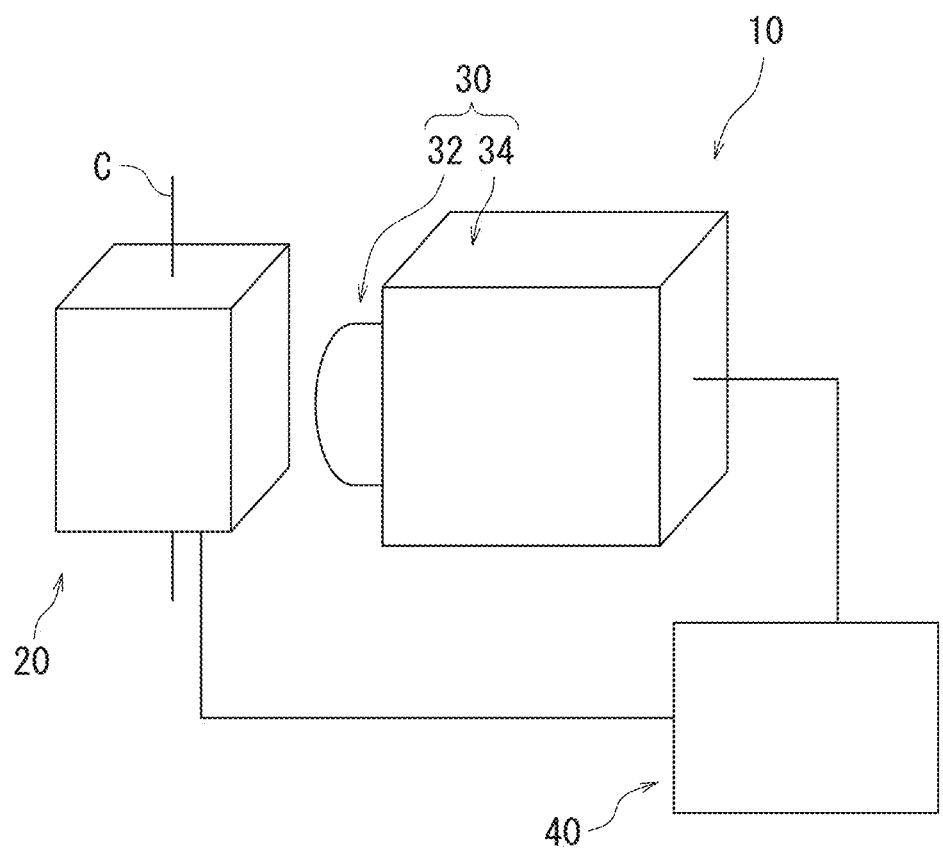
FIG. 4 is a schematic illustration of a porosity measuring device according to the present embodiment.

FIG. 4 is a schematic illustration of the porosity measuring device 10 according to the present embodiment. In the porosity measuring device 10 shown in FIG. 4, a capillary C in which the dispersion system D is filled is arranged in the vicinity of the magnetic field generating section 20. For example, the capillary C has a section orthogonal to the axial direction thereof with a shape of about 100-μm square.

The measuring section 30 includes a magnification section 32 and an imaging section 34. For example, the magnification section 32 includes an objective lens, while the imaging section 34 includes a charge coupled device (CCD). It is noted that the imaging section 34 is generally capable of measuring the size in addition to the position of the dispersoid s, but may not measure the size of the dispersoid s. For example, the imaging section 34 may measure the position of the dispersoid s by detecting the light scattered from the dispersoid s.

Figure 5:
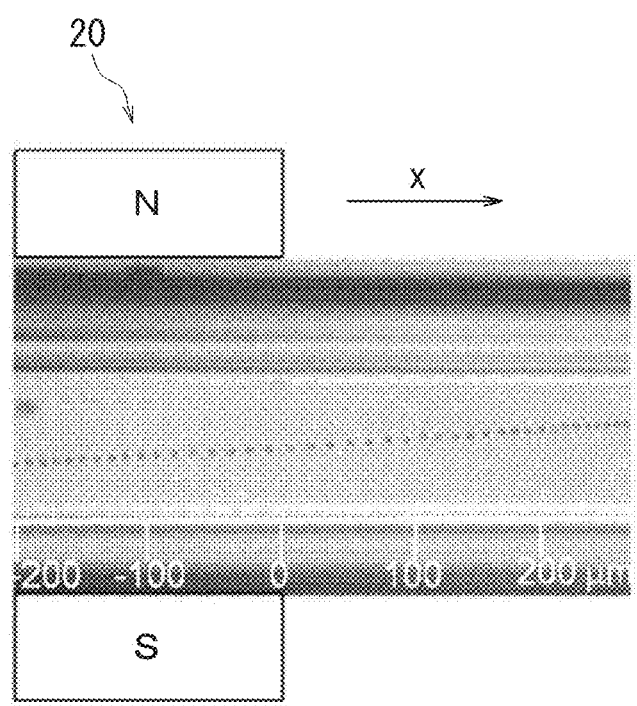
FIG. 5 is a schematic illustration showing the measurement results of the movement of the dispersoid in a porosity measuring device according to the present embodiment.

FIG. 5 shows one example of the measurement result of the movement of the dispersoid in the porosity measuring device 10. The dispersoid s herein is a polystyrene particle. The images at respective points taken at regular intervals of 0.3 seconds are overlaid.

For example, the operating section 40 obtains the magnetophoretic velocity v on the basis of the measurement result of the measuring section 30. The magnetophoretic velocity v of the dispersoid s can be expressed as follows:

$$v=\{2(\chi_s-\chi_m)r^2\}/(9\eta\mu_o)\times B(dB/dx),$$

where $\chi_s$ is a volume susceptibility of the dispersoid s; $\chi_m$ is a volume susceptibility of the dispersion medium m; r is a radius of the dispersoid s; η is a coefficient of viscosity of the dispersion medium m; $\mu_o$ is a magnetic permeability of vacuum; B is a magnetic flux density; and (dB/dx) is a gradient of the magnetic flux density. It is noted that the above equation is lead from the fact that the difference between a dispersoid s and a dispersion medium m in magnetic force that they receive in the axial direction of the capillary C is equal to a viscous resistance force.

As described above, the migration direction of the dispersoid s is determined according to each magnitude of the volume susceptibility $\chi_s$ of the dispersoid s and the volume susceptibility $\chi_m$ of the dispersion medium m. Further, as understood from the above equation, the magnetophoretic velocity v of the dispersoid s varies depending on the magnetic flux density B and/or the gradient (dB/dx) of the magnetic flux density.

Figure 6:
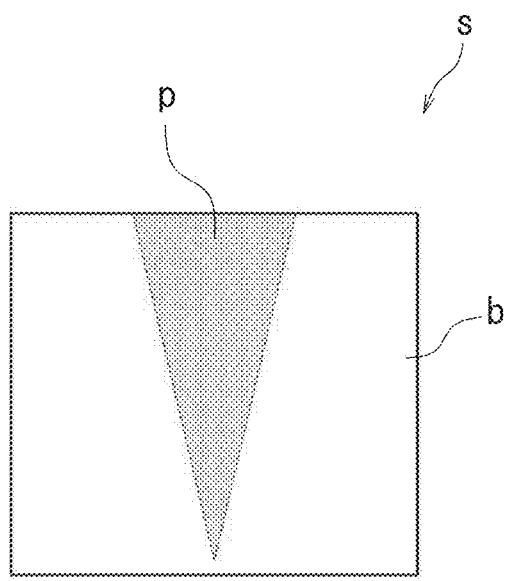
FIG. 6 is a schematic illustration showing a dispersoid with a void.

The operating section 40 obtains the volume susceptibility $\chi_s$ of the dispersoid s by utilizing the magnetophoretic velocity v obtained from the measurement result of the measuring section 30. For example, as shown in FIG. 6, the dispersoid s has a void part p filled with the dispersion medium m. Accordingly, the dispersoid s can be divided into a main body part b and the void part p.

In this case, the porosity P can be expressed as:

$$P=V_p/V_s=V_p/(V_b+V_p),$$

where $V_s$ is a volume of the dispersoid s; $V_b$ is a volume of the main body part b of the dispersoid s; and $V_p$ is a volume of the void part p of the dispersoid s. Thus, the volume $V_s$ of the dispersoid s can be expressed as a sum of the volume $V_b$ of the main body part b of the dispersoid s and the volume $V_p$ of the void part p.

$$V_s=V_b+V_p$$

It is noted that the magnetic susceptibility of the dispersoid s can be expressed as a sum of the magnetic susceptibility of the main body b of the dispersoid s and the magnetic susceptibility of the void part p of the dispersoid s. As shown in FIG. 6, where the dispersion medium m is filled in the void part p of the dispersoid s, the relationship in magnetization can be expressed as follows:

$$\chi_s V_s=\chi_b V_b+\chi_p V_p.$$

In this case, the above equation can be expressed as follows.

$$P=V_p/(V_b+V_p)=(\chi_s-\chi_b)/(\chi_p-\chi_b)$$

It is noted that where the dispersion medium m is filled in the void part p of the dispersoid s, the volume susceptibility $\chi_p$ of the void part p of the dispersoid s is equal to the volume susceptibility $\chi_m$ of the dispersion medium m.

It is noted that silica gel is generally used as a filler in liquid chromatography that is often employed in chemical analysis. The structure of silica gel can be inspected using the porosity measuring device 10 according to the present embodiment.

For example, the measurement where a silica gel particle with a diameter of about 5 μm and acetonitrile are used as the dispersoid s and the dispersion medium m, respectively, results in a magnetophoretic velocity v of 27.4 μm s$^{-1}$, $\chi_s$ can be obtained as $-7.20\pm0.02\times10^{-6}$ from this magnetophoretic velocity v. Further, as described above, where the dispersoid s and the dispersion medium m are silica gel and acetonitrile, respectively, $\chi_b$ and $\chi_m$ are $-1.36\times10^{-5}$ and $-6.76\times10^{-6}$, respectively. In this case, the porosity P is 93.3%. In addition, $V_p$ is obtained as $4.65\times10^{-11}$ cm$^3$ from the volume $V_s$ of the silica gel particle.

It is noted that any material of which size is known may be used as the dispersoid s. Alternatively, the diameter of the dispersoid s may be measured. For example, the diameter of the dispersoid s may be measured using the measuring section 30. It is noted that in order for the measuring section 30 to directly measure the diameter of the dispersoid s, the porosity measuring device 10 preferably includes a light source 50, as shown in FIG. 7.

Alternatively, the diameter of the dispersoid s may be measured by utilizing the light interference between a convex lens and a flat glass or between two optical members in a state where the dispersoid s is trapped by a gap formed between a flat glass and a flat glass. Or, the diameter of the dispersoid s may be measured by utilizing the scattered light from the dispersoid s exhibiting a Brownian motion.

Figure 7:
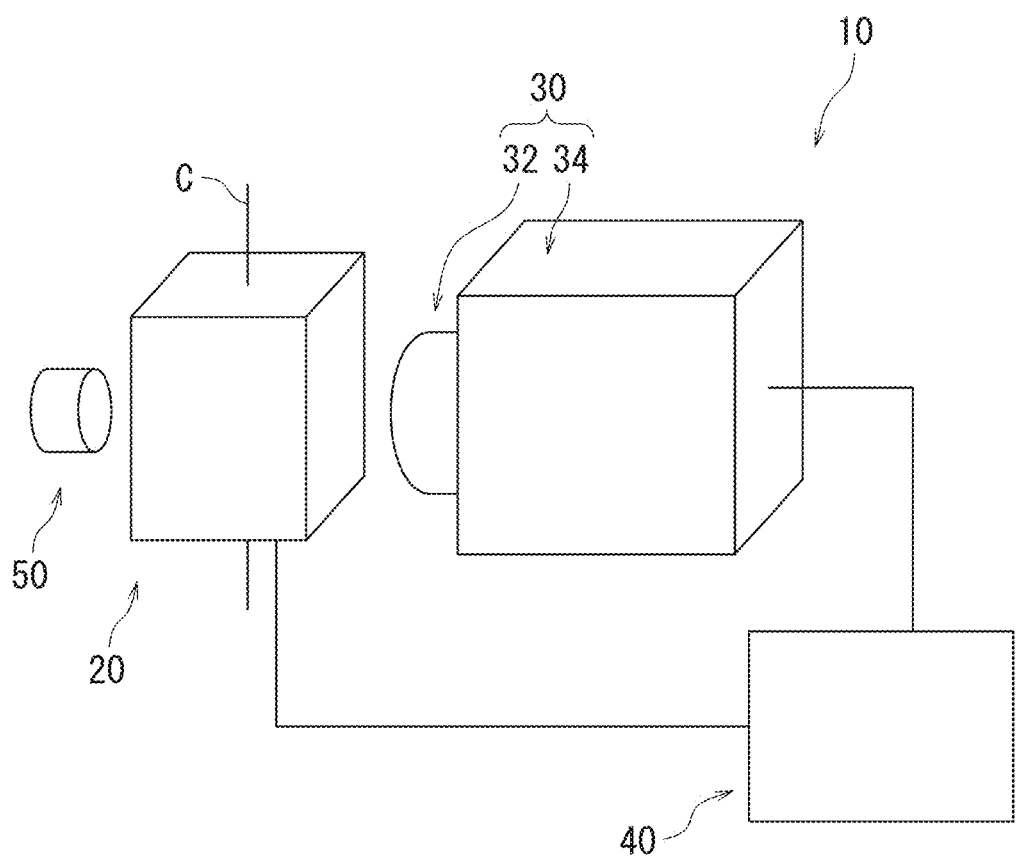
FIG. 7 is a schematic illustration of a porosity measuring device according to the present embodiment.
Figure 8:
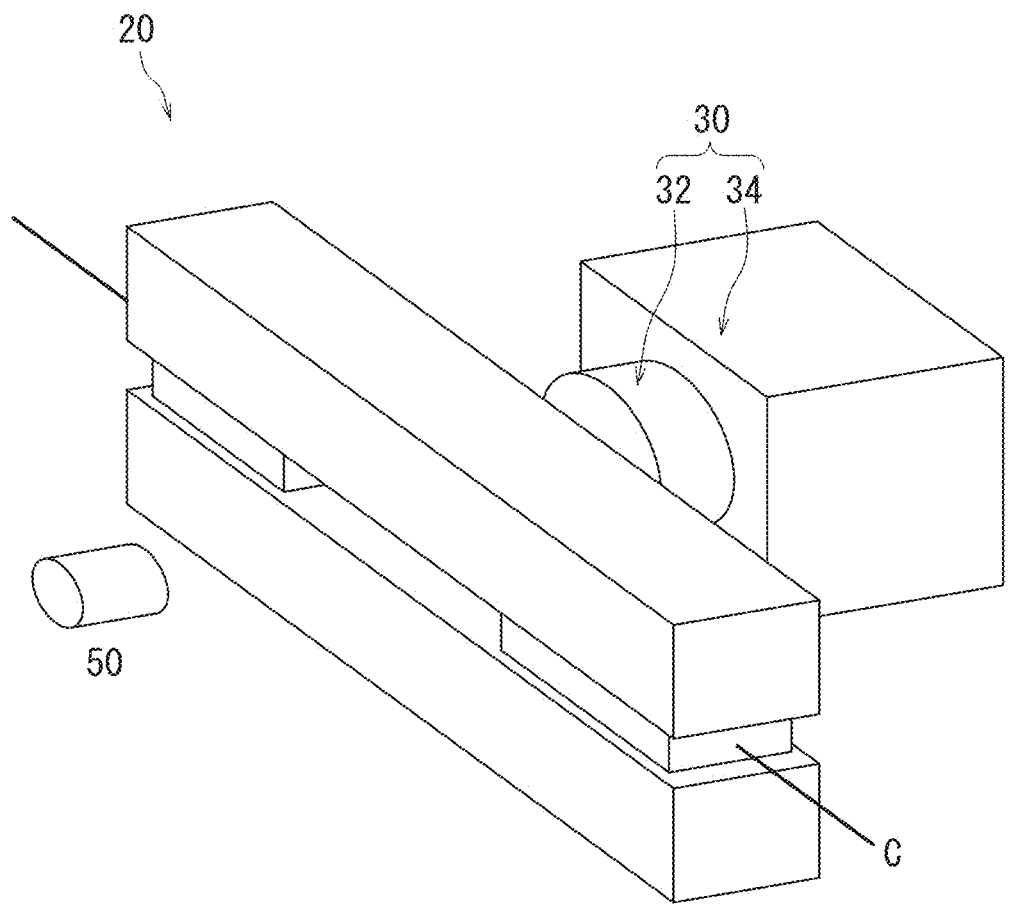
FIG. 8 is a schematic illustration of a porosity measuring device according to the present embodiment.

It is noted that in the porosity measuring devices 10 shown in FIGS. 4 and 7, the capillary C in which the dispersion system D is filled is arranged perpendicularly, which does not limit the present invention. As shown in FIG. 8, the capillary C in which is the dispersion system D is filled may be arranged horizontally in the porosity measuring device 10. For example, the magnetic field generating section 20 may generate a magnetic field with a magnetic flux density of 3 T.

Figure 9:
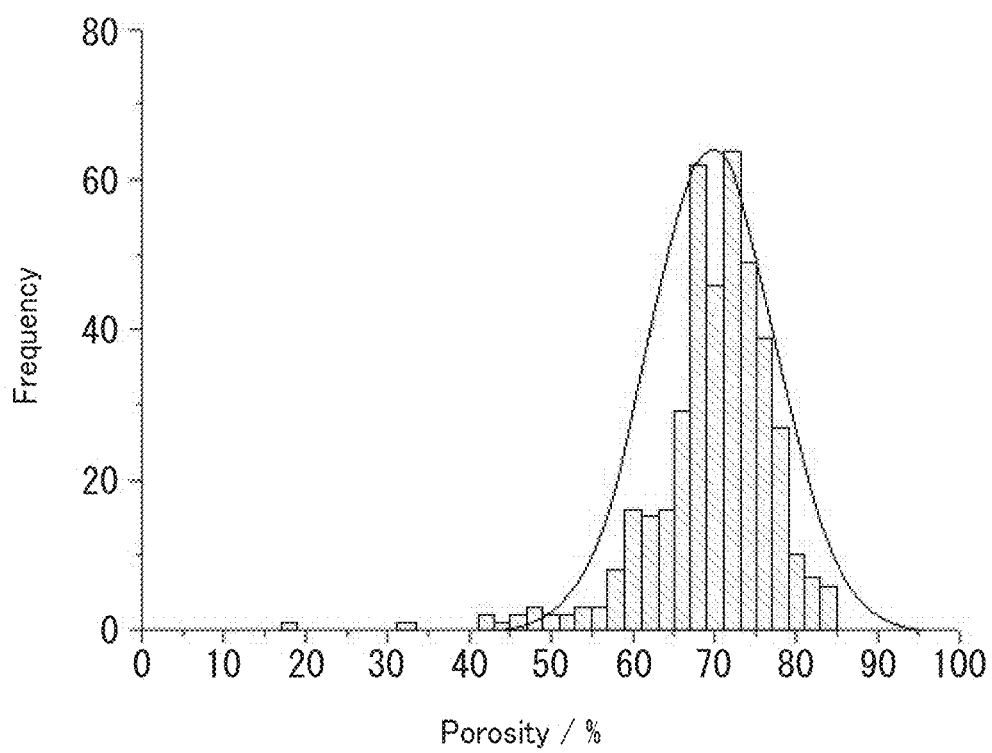
FIG. 9 is a graph representation showing the porosity measurement results in the case where acetonitrile and porous silica gel particles are used as a dispersion medium and dispersoids, respectively, in a porosity measuring device of the present embodiment.

FIG. 9 shows the measurement results of porosity in the case where acetonitrile and porous silica gel particles are used as the dispersion medium and the dispersoid, respectively, in the porosity measuring device 10 of the present embodiment. The average porosity is 69.7% according to the measurement results shown in FIG. 9. The porosity of a porous silica gel particle herein indicates a volume ratio of acetonitrile that infiltrates in the pore of the porous silica gel particle to the volume of the porous silica gel particle. It is noted that the measurement of the porosity of the porous silica gel particles by conventional nitrogen gas adsorption resulted in an average porosity of 70%, which almost agrees with the measurement results in FIG. 9. This means that acetonitrile of which amount is almost the same as that of the nitrogen gas infiltrated in the pores of the porous silica gel particles. Accordingly, it is understood that the method according to the present embodiment is valid in which the porosity of the dispersoid s is obtained from the volume susceptibility of the dispersoid s.

Further, the porosity measuring device 10 according to the present embodiment can measure the porosity of each particle, thereby easily obtaining porosity distribution. Typically, in order to obtain one average porosity, about 1000 particles must be measured. It takes about 20 minutes to measure them. It is understood that wide porosity distribution of particles with almost the same grain diameter means variation in volume of the pores of the particles.

Table 1 indicates the measurement results of the porosities of the porous silica gel particles where methanol and ethanol are used as the dispersion medium besides acetonitrile in the porosity measuring device 10 according to the present embodiment.

TABLE 1

| Solvent | Porosity (%) | Volume susceptibility/$10^{-6}$ |
|---|---|---|
| Methanol | 73.4 | −6.56 |
| Ethanol | 71.0 | −7.11 |
| Acetonitrile | 69.7 | −6.74 |

As understood from Table 1, the use the organic solvents of these three types brought almost the same results. Thus, even with the use of different solutions, the porosity of the dispersoid s can be measured.

It is noted that change in volume susceptibilities of the dispersoids s by chemical change of the dispersoid s may change the direction of magnetophoresis of the dispersoids s relative to the flow of the dispersion medium m. For example, when the dispersoids s wholly form radicals by chemical change, the dispersoids s become paramagnetic. For this reason, the magnitude relationship between the volume susceptibilities of the dispersoids s and the volume susceptibility of the dispersion medium m may be reversed. In this case, the change of the dispersoids s reverses the direction of magnetophoresis of the dispersoids s. By contrast, in the case where almost all part of the dispersoids s is not subjected to chemical change, and only part thereof forms radicals, the dispersoid s may remain diamagnetic as a whole, resulting in reduction in magnetic susceptibility of the dispersoids s. Accordingly, the progress where the dispersoids s form radicals can be monitored on the basis of the magnetophoretic motion of the dispersoids s, that is, on the basis of variation in magnetic susceptibilities of the dispersoids s.

It is noted that technically, reversal of the direction of magnetophoresis of the dispersoid s may be caused when the density of the dispersoid s varies greatly to reverse the magnitude relationship between the volume susceptibility of the dispersoid s and the volume susceptibility of the dispersion medium m. However, whether or not the density of the dispersoid s varies greatly can be inspected by monitoring the change of the dispersoid s by the measuring section 30.

In this way, with the porosity measuring device 10 according to the present embodiment, timing when the dispersoid s forms radicals can be specified, and change to the radical can be visualized. It is noted that change (e.g., chemical change) of the dispersoid s may be induced in a state where the porosity measuring device 10 is installed or be induced outside the porosity measuring device 10.

It is noted that the dispersoid s is divided into two parts of the main body part b and the void part p in the above description, which imposes no limitation on the present invention. The dispersoid s may be divided into three or more parts. For example, the dispersoid s may be subjected to surface treatment in order to increase its hydrophilicity. In this case, a part different from the main body part of the dispersoid s is formed on the surface of the dispersoid s.

Figure 10:
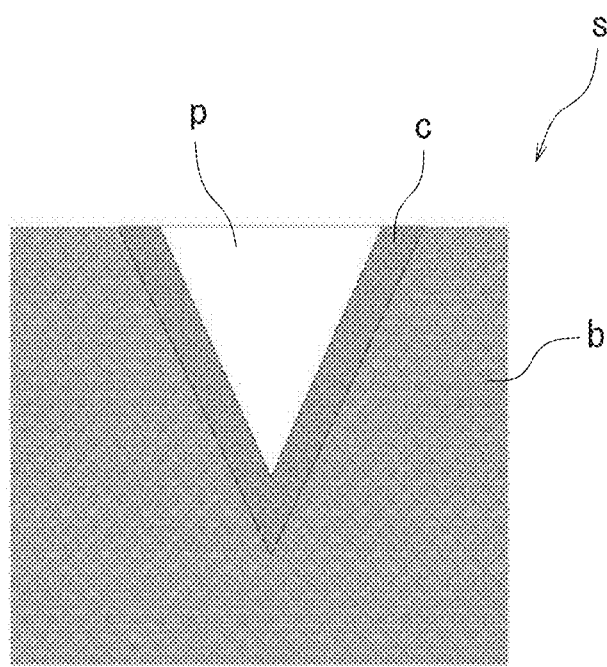
FIG. 10 is a schematic illustration showing a dispersoid with a void.

As shown in FIG. 10, a dispersoid s is divided into three parts of a main body part b, a surface part c, and a void part p. The dispersoid s including these three parts corresponds to, for example, silica gel with a void of which surface is modified with an octadecylsilyl (ODS) group ($C_{18}H_{37}Si$). In this case, the volume of the dispersoid s is expressed in the following equation:

$$V_s = V_b + V_c + V_p,$$

where $V_s$ is a volume of the dispersoid s; $V_b$ is a volume of the main body part b of the dispersoid s; $V_c$ is a volume of the surface part c of the dispersoid s; and $V_p$ is a volume of the void part p of the dispersoid s.

Further, the magnetic susceptibility of the dispersoid s is expressed as a sum of the magnetic susceptibility of the body main part b of the dispersoid s, the magnetic susceptibility of the surface part c of the dispersoid s, and the magnetic susceptibility of the void part b of the dispersoid s:

$$\chi_s V_s = \chi_b V_b + \chi_c V_c + \chi_p V_p,$$

where $\chi_s$ is a volume susceptibility of the dispersoid s; $\chi_b$ is a volume susceptibility of the body main part b of the dispersoid s; $\chi_c$ is a volume susceptibility of the surface part c of the dispersoid s; and $\chi_p$ is a volume susceptibility of the void part p of the dispersoid s.

It is noted that the above volume relationship is expressed as:

$$V_c = V_s - V_b - V_p.$$

A measurement value can be used as $V_b$.

Furthermore, the porosity P is expressed as follows:

$$P = V_p / V_s = V_p / (V_b + V_c + V_p).$$

This porosity P can be expressed as follows using the above relationship of magnetization:

$$P = (\chi_c - \chi_s)/(\chi_c - \chi_m) - (\chi_c - \chi_b) \times V_b / ((\chi_c - \chi_m) \times V_s).$$

For example, when silica gel particles with a diameter of 5 μm subjected to surface modification with the ODS group is dispersed in acetonitrile, $\chi_s$ can be obtained as $-7.82 \times 10^{-6}$ from the magnetophoretic velocity of the dispersoid s. The volume susceptibility $\chi_p$ of the void part p of the dispersoid s is equal to the volume susceptibility $\chi_m$ of the dispersion medium m, $-6.76 \times 10^{-6}$. Further, from the value in a reference, $\chi_b$ and $\chi_c$ are $-1.56 \times 10^{-5}$ and $-8.43 \times 10^{-6}$, respectively. Moreover, with similar silica gel not subjected to surface modification, the volume $V_b$ of the main body part b of the dispersoid s is $6.06 \times 10^{-11}$ cm$^3$, and the volume $V_s$ of the dispersoid s is $9.04 \times 10^{-10}$ cm$^3$. From the above, the porosity P ($=V_p/V_s$) can be obtained as 0.64 (64%). According to this result, it can be determined that the volume $V_c$ of the surface part c of the dispersoid s subjected to surface modification is $2.66 \times 10^{-10}$ cm$^3$, and the volume $V_p$ of the void part p of the dispersoid s is $5.83 \times 10^{-10}$ cm$^3$. It is noted that as understood when comparing the descriptions with reference to FIGS. 6 and 10, the dispersoid s may include another part in addition to the main body part b and the void part p.

Furthermore, comparison between the porosity distribution of the dispersoids s after surface modification and the porosity distribution of the dispersoids s before the surface modification can results in inspection of the uniformity in the surface modification. Specifically, when the variance of the porosity distribution of dispersoids s after surface modification is almost the same as that of the porosity distribution of the dispersoids s after the surface modification, the surface modification is considered to be almost uniformly performed. By contrast, when the variance of the porosity distribution of dispersoids s after surface modification is rather larger than that of the porosity distribution of the dispersoids s before the surface modification, the surface modification is considered to be non-uniformly performed.

Figure 11:
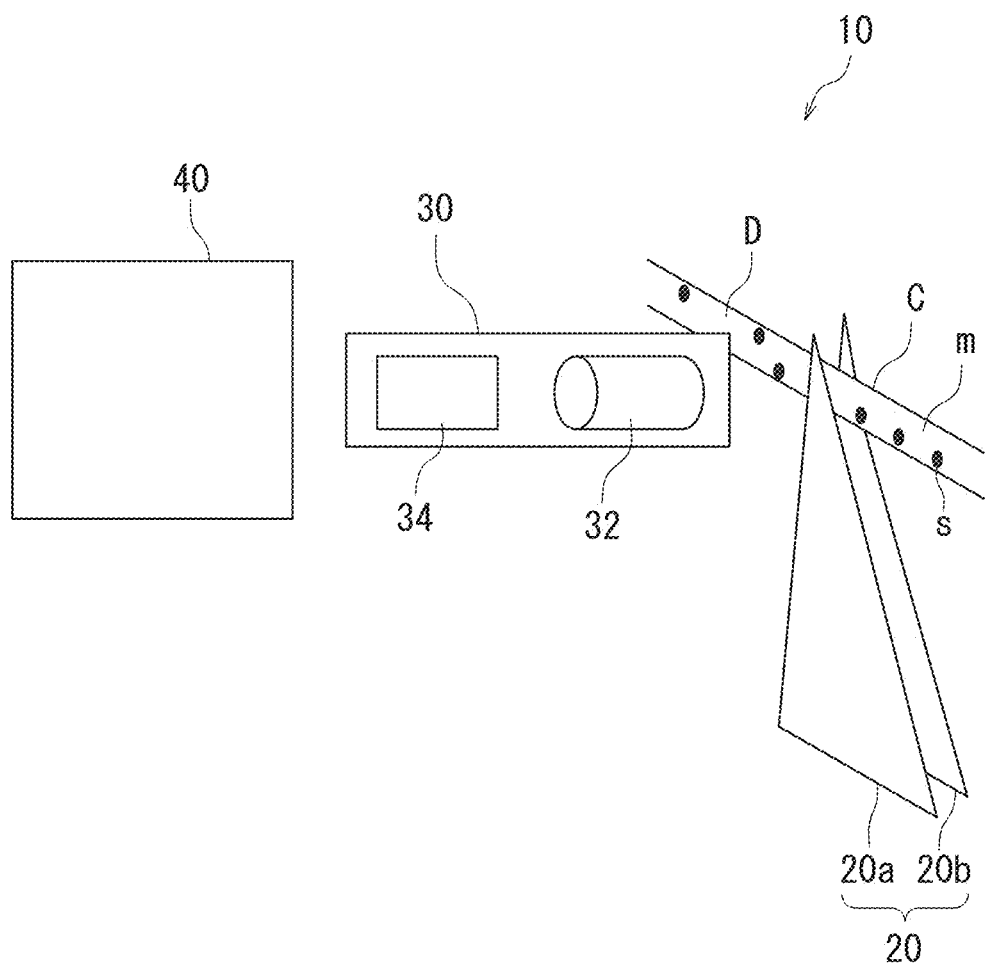
FIG. 11 is a schematic illustration of a porosity measuring device in the present embodiment.
Figure 12:
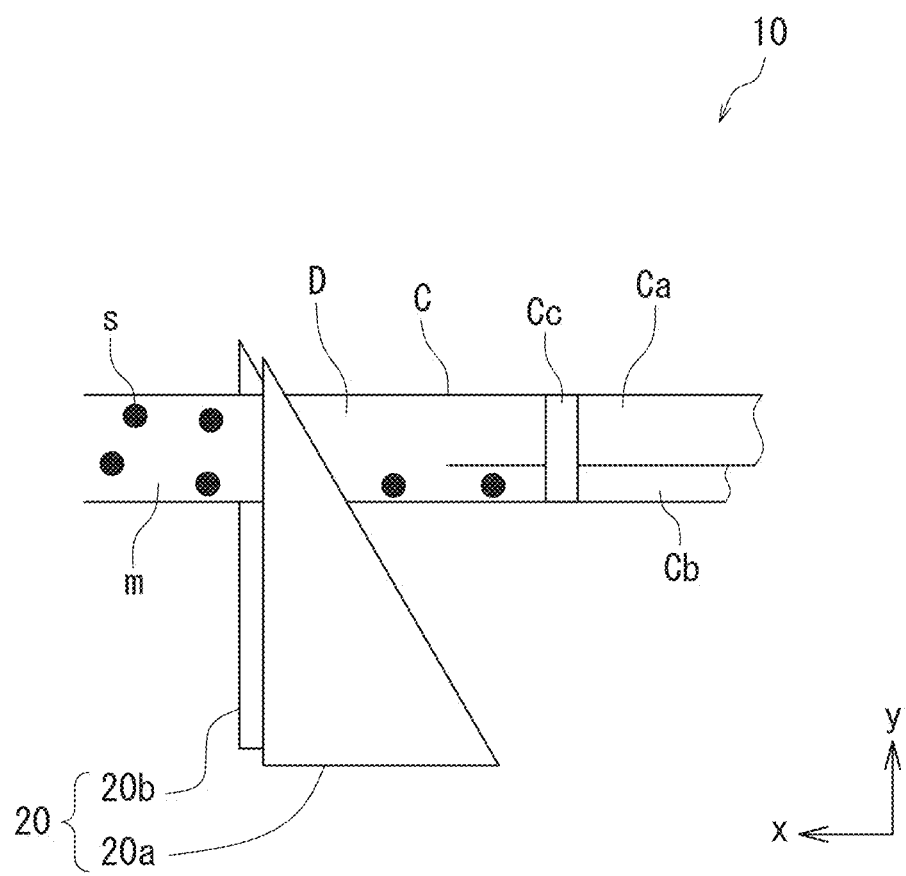
FIG. 12 is a schematic illustration in which part of the porosity measuring device according to the present embodiment is enlarged.
Figure 13:
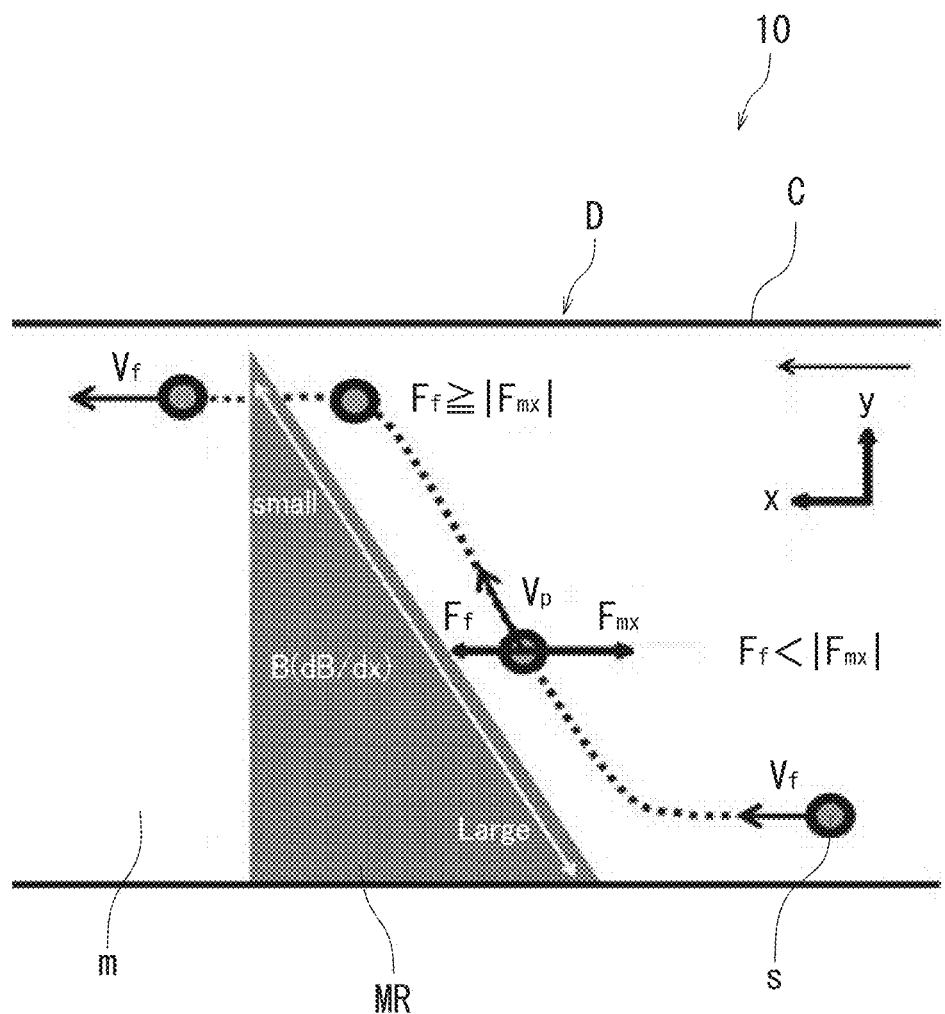
FIG. 13 is a schematic illustration in which part of the porosity measuring device according to the present embodiment is enlarged.

It is noted that the dispersoids s can be distinguished according to their magnetic susceptibilities or their porosities. With reference to FIGS. 11-13, one embodiment of the porosity measuring device 10 will now be described which is capable of distinguishing dispersoids s according to their magnetic susceptibilities or their porosities.

FIG. 11 is a schematic illustration of a porosity measuring device 10 in the present embodiment. This porosity measuring device 10 includes a magnetic field generating section 20, a dispersoid measuring section 30, and an operating section 40. The dispersoid measuring section 30 includes a magnification section 32 and an imaging section 34. The porosity measuring device 10 shown in FIG. 11 has the same configuration as the porosity measuring devices 10 described above with reference to FIG. 1 or 4, except that the magnetic field generating section 20 generates a magnetic field so that the positions of dispersoids s distributed in a dispersion medium m differ according to the volume susceptibilities of the dispersoids s. Hence, duplicate description may be omitted in order to avoid redundancy.

A dispersion system D in which the dispersoids s are dispersed in the dispersion medium m is filled in a capillary C in the vicinity of the magnetic field generating section 20. The volume susceptibility of each dispersoids s herein is smaller than the volume susceptibility of the dispersion medium m. For example, the dispersoids s are polystyrene particles, while the dispersion medium m is a $MnCl_2$ solution.

The magnetic field generating section 20 includes pole pieces 20a, 20b. The pole pieces 20a, 20b interpose the capillary C. The capillary C is arranged across the space defined by the pole pieces 20a, 20b.

The pole pieces 20a, 20b generate a magnetic field within the capillary C. The pole pieces 20a, 20b generate the magnetic field, which is different in strength according to the position in the width direction (y direction) of the capillary C. The pole pieces 20a, 20b herein are each triangular in shape and have almost the same shape and size. The area where the pole pieces 20a, 20b overlap with the capillary C varies monotonically along the width direction of the capillary C.

FIG. 12 is a schematic illustration showing part of the porosity measuring device 10 shown in FIG. 11 on an enlarged scale. The capillary C is connected to a dispersion medium inlet pipe Ca and a dispersoid inlet pipe Cb through a sealing portion Cc. The diameter of the capillary C is larger than those of the dispersion medium inlet pipe Ca and the dispersoid inlet pipe Cb. Further, the diameter of the dispersion medium inlet pipe Ca is larger than that of the dispersoid inlet pipe Cb typically. The dispersoid inlet pipe Cb is arranged so as to correspond to a region where the overlap area between the pole pieces 20a, 20b and the capillary C is comparatively large in the width direction of the capillary C.

The pole pieces 20a, 20b are each arranged so that one of two sides forming a right angle is in parallel to the longitudinal direction of the capillary C (direction in which the dispersion medium flows: x direction), while the other side of the two sides forming the right angle is in parallel to the width direction of the capillary C. The pole pieces 20a, 20b apply the magnetic field, of which magnitude differs according to the position in the perpendicular direction (width direction of the capillary C). For example, the capillary C has a diameter of 300 μm (length in the width direction). Each of the pole pieces 20a, 20b is a right triangle in shape with sides of 3 mm, 4 mm, and 5 mm The dispersion medium m moves from the dispersion medium inlet pipe Ca to the capillary C and flows in the longitudinal direction of the capillary C (x direction). The dispersoids s move from the dispersoid inlet pipe Cb to the capillary C. The dispersoids s flowing into the capillary C through the dispersoid inlet pipe Cb merge into the dispersion medium m flowing in the capillary C through the dispersion medium inlet pipe Ca. Thereafter, the dispersoids s move together with the dispersion medium m to reach the vicinity of a magnetic field forming region formed by the pole pieces 20a, 20b.

FIG. 13 is a schematic illustration of part of the porosity measuring device 10 shown in FIGS. 11 and 12 on an enlarged scale. FIG. 13 schematically shows the magnetic field forming region MR formed inside the capillary C by the pole pieces 20a, 20b.

The dispersion medium m flows in the longitudinal direction (x direction) of the capillary C. The dispersoids s receive fluid drive power $F_f$ from the dispersion medium m. The dispersoids s move at a flow velocity $V_f$ up to the vicinity of the pole pieces 20a, 20b. Technically, it is preferable to consider that the flow of the dispersion medium m in the capillary C is a laminar flow.

Upon reaching the vicinity of the pole pieces 20a, 20b, the dispersoids s receive the magnetic force of the pole pieces 20a, 20b. Here, the volume susceptibility of each dispersoid s are smaller than the volume susceptibility of the dispersion medium m. Accordingly, the magnetic force acts in the direction that pushes back the dispersoids s against the flow of the dispersion medium m. The magnetic force that the dispersoids s receive differs according to the position in the width direction of the capillary C. The component $F_{mx}$ in the x direction of the magnetic force can be expressed as follows:

$$F_{mx} = -\{4(\chi_s - \chi_m)\pi r^3\}/(3\mu_o) \times B(dB/dx).$$

Referring to the magnetic field formation region MR of the porosity measuring device 10 shown in FIG. 13, the magnitude of B(dB/dx) differs according to the position in the width direction in the capillary C. Accordingly, in the width direction of the capillary C, the value of B(dB/dx) is large at a point where the overlap area between the pole pieces 20a, 20b and the capillary C is large and is small at a point where the overlap area between the pole pieces 20a, 20b and the capillary C is small. Thus, even with the identical dispersoids s, the larger the overlap area between the pole pieces 20a, 20b and the capillary C in the width direction of the capillary C is, the larger the component $F_{mx}$ in the x direction of the magnetic force is. The smaller the overlap area with the capillary C is, the smaller the component $F_{mx}$ in x direction of the magnetic force is.

The dispersoids s reach the vicinity of the magnetic field formation region MR formed by the pole pieces 20a, 20b to receive the magnetic force larger than the fluid drive power $F_f$. Technically, the dispersoids s receive the magnetic force in the direction orthogonal to the hypotenuse of the magnetic field formation region MR from the magnetic field formation region MR to advance in the direction expressed as a sum of the vectors of the fluid drive power $F_f$ and the magnetic force. Typically, the direction of the sum of the vectors is almost in parallel with each hypotenuse (of the right triangles) of the pole pieces 20a, 20a. Therefore, the dispersoids s move in the diagonal direction almost in parallel with each hypotenuse (of the right triangles) of the pole pieces 20a, 20b.

As the dispersoids s move diagonally, the component $F_{mx}$ in the x direction of the magnetic force that the dispersoids s receive decreases. When the magnetic force $F_{mx}$ that the dispersoids s receive becomes almost equal to the fluid drive power $F_f$ from the dispersion medium m, the dispersoids s pass through the magnetic field formation region MR formed by the pole pieces 20a, 20b.

For example, where the volume susceptibility of each dispersoids s is comparatively small, that is, where the difference in volume susceptibility between the dispersion medium m and the dispersoids s is comparatively large, the magnetic force $F_{mx}$ is comparatively large. Accordingly, unless the dispersoids s move in the width direction of the capillary C comparatively long, they cannot pass through the magnetic field formation region MR. On the contrary, where the volume susceptibility of each dispersoid s is comparatively large, that is, where the difference in volume susceptibility between the dispersion medium m and the dispersoids s is comparatively small, the magnetic force Fmx is comparatively small. Accordingly, even when the dispersoids s move in the width direction of the capillary C comparatively short, they can pass through the magnetic field formation region MR. It is noted that though not shown herein, the capillary C may be connected to at least one dispersoid taking pipe for separating and taking out the distinguished dispersoids s.

In this manner, the porosity measuring device 10 can distinguish the dispersoids s by moving the dispersoids s in the width direction of the capillary C according to the volume susceptibility of the dispersoids s. In this case, the magnetic field formation region MR formed by the pole pieces 20a, 20b functions as a selection region of the dispersoids s. According to the porosity measuring device 10 of the present embodiment, even when the width of the capillary C is comparatively small, the dispersoids s can be distinguished efficiently. Further, in the porosity measuring device 10 of the present embodiment, the dispersoids s move together with the dispersion medium m. Thus, a comparatively large amount of dispersoids s can be easily distinguished.

It is noted that the volume susceptibility of a dispersoid s is relevant to the porosity of the dispersoid s, as described above. Accordingly, distinguishing the dispersoids s according to their volume susceptibilities can result in distinguishing the dispersoids s according to their porosities. For example, when dispersoids s that are same in composition and grain size are distinguished according to the volume susceptibilities of the dispersoids s, the dispersoids s are distinguished at positions different in the width direction of the capillary C according to the porosity. Accordingly, the dispersoids s with desired porosities can be obtained according to the different positions in the width direction in the capillary C.

INDUSTRIAL APPLICABILITY

According to the present invention, the porosity of each dispersoid can be measured. The porosity measuring device and/or the porosity measuring method according to the present invention are applicable to cosmetic fields, medical product fields, environmental fields, and nanoparticle manufacture.

REFERENCE SINGS LIST 10 porosity measuring device
20 magnetic field generating section
30 dispersoid measuring section
40 operating section

The invention claimed is:

1. A porosity measuring device comprising:
   a magnetic field generating section;
   a dispersoid measuring section configured to measure movement of a dispersoid dispersed in a dispersion medium in a state where a magnetic field is generated by the magnetic field generating section; and
   an operating section configured to obtain a porosity of the dispersoid on the basis of a measurement result of the dispersoid measuring section,
   wherein the operating section obtains a magnetophoretic velocity of the dispersoid from the measurement result of the dispersoid measuring section, obtains a volume susceptibility of the dispersoid from the magnetophoretic velocity of the dispersoid, and obtains the porosity of the dispersoid on the basis of the volume susceptibility of the dispersoid, a volume relationship of the dispersoid, and a relationship in magnetization of the dispoersoid.

2. The device of claim 1, wherein
the dispersoid measuring section includes:
   an optical lens configured to magnify the dispersoid dispersed in the dispersion medium; and
   an imaging section configured to image the dispersoid magnified by the optical lens.

3. The device of claim 1, wherein
the magnetic field generating section is configured to generate the magnetic field so that a position of the dispersoid dispersed in the dispersion medium differs according to a volume susceptibility of the dispersoid.

4. A porosity measuring method comprising:
measuring movement of a dispersoid dispersed in a dispersion medium in a state where a magnetic field is generated; and
obtaining a porosity of the dispersoid on the basis of a measurement result of the movement of the dispersoid,
wherein the obtaining a porosity of the dispersoid includes:
   obtaining a magnetophoretic velocity of the dispersoid from the measurement result of the movement of the dispersoid,
   obtaining a volume susceptibility of the dispersoid from the magnetophoretic velocity of the dispersoid; and
   obtaining the porosity of the dispersoid on the basis of the volume susceptibility of the dispersoid, a volume relationship of the dispersoid, and a relationship in magnetization of the dispoersoid.

5. The method of claim 4, wherein
in the measuring movement of the dispersoid, the magnetic field is generated so that a position of the dispersoid dispersed in the dispersion medium differs according to the volume susceptibility of the dispersoid.

6. The method of claim 4, wherein the dispersoid includes a silica gel particle.

7. The method of claim 4, wherein the dispersion medium includes acetonitrile.

* * * * *